US009229338B2

(12) United States Patent
Van De Kerkhof et al.

(10) Patent No.: US 9,229,338 B2
(45) Date of Patent: Jan. 5, 2016

(54) SUBSTRATE, A METHOD OF MEASURING A PROPERTY, AN INSPECTION APPARATUS AND A LITHOGRAPHIC APPARATUS

(75) Inventors: Marcus Adrianus Van De Kerkhof, Helmond (NL); Maurits Van Der Schaar, Eindhoven (NL); Hendrik Jan Hidde Smilde, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 1134 days.

(21) Appl. No.: 13/059,405

(22) PCT Filed: Jul. 27, 2009

(86) PCT No.: PCT/EP2009/005419
§ 371 (c)(1),
(2), (4) Date: May 12, 2011

(87) PCT Pub. No.: WO2010/025793
PCT Pub. Date: Mar. 11, 2010

(65) Prior Publication Data
US 2011/0205518 A1    Aug. 25, 2011

Related U.S. Application Data

(60) Provisional application No. 61/095,112, filed on Sep. 8, 2008.

(51) Int. Cl.
*G01B 11/00* (2006.01)
*G03B 27/32* (2006.01)
(Continued)

(52) U.S. Cl.
CPC ........ *G03F 7/70683* (2013.01); *G03F 7/70633* (2013.01); *G03F 9/70* (2013.01);
(Continued)

(58) Field of Classification Search
CPC ............ G03F 7/70633; G03F 7/70675; G03F 7/70683; G03F 9/00; G03F 9/70; G03F 9/7046; G03F 9/7049; G03F 9/7073; G03F 9/7076; G03F 9/708; G03F 2009/005; H01L 23/544
USPC .......................... 257/797; 355/53, 67, 68, 77; 356/399–401, 521, 614–622; 382/287; 428/172, 127
See application file for complete search history.

(56) References Cited

U.S. PATENT DOCUMENTS 6,262,487 B1 *  7/2001  Igarashi et al. ............... 257/758
6,844,918 B2    1/2005  Koren et al.
(Continued)

FOREIGN PATENT DOCUMENTS

| EP | 1 477 860 A1 | 11/2004 |
| EP | 1 628 164 A2 | 2/2006 |
| EP | 1 677 158 A2 | 7/2006 |

OTHER PUBLICATIONS

International Search Report and Written Opinion directed to related International Patent Application No. PCT/EP2009/005419, The International Bureau of WIPO, Geneva, Switzerland, mailed Mar. 17, 2011; 11 pages.
Notice of Allowance mailed Oct. 2, 2015 for U.S. Appl. No. 14/825,765, filed Aug. 13, 2015; 10 pages.

*Primary Examiner* — Colin Kreutzer
(74) *Attorney, Agent, or Firm* — Sterne, Kessler, Goldstein & Fox P.L.L.C.

(57) ABSTRACT

Scatterometry for measuring overlay. A second set of superimposed gratings are superposed over a first set of superimposed gratings. The second set of gratings have a different periodicity from the first set of gratings or a different orientation. Consequently the first order diffraction pattern from the second set of superimposed gratings can be distinguished from the first order diffraction pattern from the first set of superimposed gratings.

5 Claims, 5 Drawing Sheets

(51) Int. Cl.
*G03B 27/54* (2006.01)
*G03B 27/74* (2006.01)
*H01L 23/28* (2006.01)
*G03F 7/20* (2006.01)
*G03F 9/00* (2006.01)
*H01L 23/544* (2006.01)

(52) U.S. Cl.
CPC ............ *G03F 9/7046* (2013.01); *G03F 9/7076* (2013.01); *H01L 23/544* (2013.01); *H01L 2924/0002* (2013.01); *Y10T 428/24612* (2015.01)

(56) References Cited

U.S. PATENT DOCUMENTS

| | | | |
|---|---|---|---|
| 7,355,675 | B2 | 4/2008 | Lalbahadoersing et al. |
| 2004/0233440 | A1* | 11/2004 | Mieher et al. ............... 356/401 |
| 2006/0138682 | A1 | 6/2006 | Van Haren |
| 2006/0222962 | A1 | 10/2006 | Chen et al. |
| 2008/0212097 | A1 | 9/2008 | Mos et al. |
| 2009/0115987 | A1 | 5/2009 | Butler et al. |

* cited by examiner

SUBSTRATE, A METHOD OF MEASURING A PROPERTY, AN INSPECTION APPARATUS AND A LITHOGRAPHIC APPARATUS

CROSS-REFERENCE TO RELATED APPLICATIONS

This application claims the benefit of U.S. provisional application 61/095,112, which was filed on Sep. 8, 2008, and which is incorporated herein in its entirety by reference.

FIELD

Embodiments of the present invention relate to methods of inspection usable, for example, in the manufacture of devices by lithographic techniques and to methods of manufacturing devices using lithographic techniques. Embodiments of the present invention have particular relevance to an inspection method for measuring the property of a substrate, a substrate for use in the method, an inspection apparatus for performing the method and a lithographic apparatus.

RELATED ART

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of a specialized inspection tool is a scatterometer in which a beam of radiation is directed onto a target in or on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Existing scatterometers use a plurality of superimposed gratings to determine the overlay error. The superimposed gratings do not form part of the circuit pattern and therefore occupy an area of the substrate which cannot then be used as part of the circuit pattern. However, space on the substrate is at a premium and it is therefore desirable to reduce the area occupied by the targets used to determine overlay error.

SUMMARY

It is desirable to reduce the area occupied by the targets used for measuring the overlay error.

According to an aspect of the invention, there is provided a substrate including a first plurality of superimposed patterns and a second plurality of superimposed patterns, the second plurality of superimposed patterns in turn being superimposed over the first plurality of superimposed patterns, the first plurality of superimposed patterns having a periodicity in a first direction and the second plurality of superimposed patterns having a periodicity in a second direction. The first direction and the second direction are different from each other such that within an image of respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided a substrate including a first plurality of superimposed patterns and a second plurality of superimposed patterns, the second plurality of patterns being in turn superimposed on the first plurality of patterns. The first plurality of patterns are periodic patterns, the patterns having a period of d, and the second plurality of patterns are also periodic patterns and have a period which is different from d such that within an image of respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided a method of measuring a property of a substrate. The method includes exposing a first pattern, exposing a second pattern superimposed over the first pattern to form a first plurality of patterns with the first pattern, the first plurality of patterns having a periodicity in a first direction, exposing a third pattern, exposing a fourth pattern superimposed over the third pattern to form a second plurality of patterns with the third pattern, the second plurality of patterns having a periodicity in a second direction, projecting radiation onto the second plurality of patterns, detecting the radiation reflected by the substrate to form a detected image, and determining the property from the reflected radiation. The second plurality of patterns is superimposed on the first plurality of patterns. The first and second directions are different from each other such that within the detected image in respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided a method of measuring a property of a substrate. The method includes exposing a first pattern, exposing a second pattern superimposed over the first pattern to form a first plurality of patterns with the first pattern, the first plurality of patterns being periodic with a periodicity of d, exposing a third pattern, exposing a fourth pattern superimposed over the third pattern to form a second plurality of patterns with the third pattern, the second plurality of patterns being periodic and having a period different to d, projecting radiation onto the second plurality of patterns, detecting the radiation reflected by the substrate, and determining the property from the reflected radiation. The second plurality of patterns is superimposed over the first plurality of patterns. The periods of the first and second plurality of patterns are such that within an image of respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided an inspection apparatus configured to measure a property of a substrate, the apparatus including a radiation projector configured to project radiation onto the substrate, a high numerical aperture lens, a detector configured to detect the radiation beam reflected from a surface of the substrate, and a substrate. The substrate includes a first plurality of superimposed patterns and a second plurality of superimposed patterns, the second plurality of superimposed patterns being superimposed over the first plurality of superimposed patterns, the first plurality of superimposed patterns having a periodicity in a first direction and the second plurality of superimposed patterns having a periodicity in a second direction. The first and second directions are different from each other such that within an image of respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided an inspection apparatus configured to measure a property of a substrate, the apparatus including a radiation projector configured to project radiation onto said substrate, a high numerical aperture lens, a detector configured to detect the radiation beam reflected from a surface of the substrate, and a substrate. The substrate includes a first plurality of superimposed patterns and a second plurality of superimposed patterns, the second plurality of patterns being superimposed on the first plurality of patterns. The first plurality of patterns are periodic patterns, the patterns having a period of d, the second plurality of patterns also being periodic patterns and having a period different to d such that such that within an image of respective diffraction patterns produced by radiation reflected by each of the first plurality of superimposed patterns and the second plurality of superimposed patterns, the diffraction patterns of at least one order corresponding to each of the first and second pluralities of superimposed patterns are spatially distinguishable from each other.

According to a further aspect of the invention there is provided a lithographic apparatus including an illumination optical system arranged to illuminate a pattern, a projection optical system arranged to project an image of the pattern on to a substrate, and an inspection apparatus as described above.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
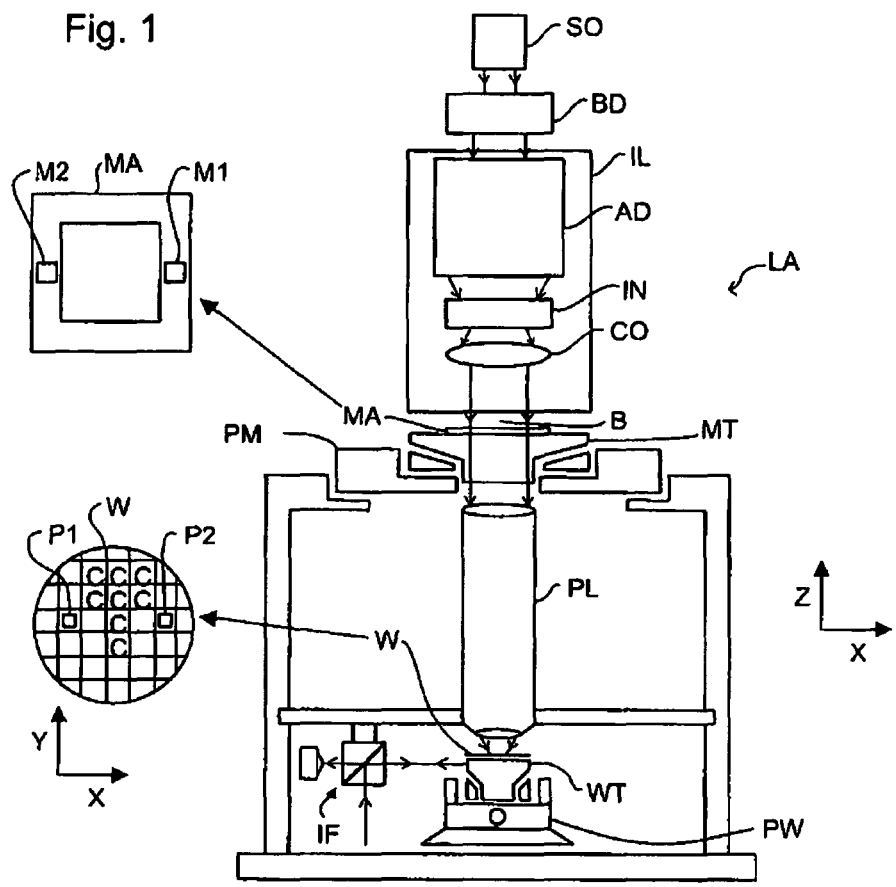
FIG. 1 depicts a lithographic apparatus that may be used in an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

Detailed Description

The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The lithographic apparatus includes: an illumination system (illuminator) IL configured to condition a radiation beam B (e.g., DUV or EUV radiation); a support structure (e.g., a mask table) MT configured to support a patterning device (e.g., a mask, a reticle, or a dynamic patterning device) MA and connected to a first positioner PM configured to accurately position the patterning device MA; and a substrate table (e.g., a wafer table) WT configured to hold a substrate (e.g., a resist coated wafer) W and connected to a second positioner PW configured to accurately position substrate W. The lithographic apparatus also has a projection system PS configured to project a pattern imparted to radiation beam B by patterning device MA onto a target portion (e.g., comprising one or more dies) C of substrate W. In the lithographic apparatus patterning device MA and projection system PS are transmissive, but alternatively could be reflective.

Illumination system IL may include various types of optical components, such as refractive, reflective, magnetic, electromagnetic, electrostatic or other types of optical components, or any combination thereof, for directing, shaping, or controlling radiation B.

Support structure MT holds patterning device MA in a manner that depends on the orientation of patterning device MA, the design of the lithographic apparatus, and other conditions, such as for example whether or not patterning device MA is held in a vacuum environment. Support structure MT may use mechanical, vacuum, electrostatic or other clamping techniques to hold patterning device MA. Support structure MT may be a frame or a table, for example, which may be fixed or movable, as required. Support structure MT may ensure that the patterning device is at a desired position, for example with respect to projection system PS.

The term "patterning device" MA should be broadly interpreted as referring to any device that may be used to impart a radiation beam B with a pattern in its cross-section, such as to create a pattern in target portion C of substrate W. The pattern imparted to radiation beam B may correspond to a particular functional layer in a device being created in target portion C, such as an integrated circuit.

Patterning device MA may be transmissive or reflective. Examples of patterning devices MA include reticles, masks, programmable mirror arrays, and programmable LCD panels. Masks are well known in lithography, and include mask types such as binary, alternating phase shift, and attenuated phase shift, as well as various hybrid mask types. An example of a programmable mirror array employs a matrix arrangement of small mirrors, each of which may be individually tilted so as to reflect an incoming radiation beam in different directions. The tilted mirrors impart a pattern in radiation beam B which is reflected by the mirror matrix.

The term "projection system" PS may encompass any type of projection system, including refractive, reflective, catadioptric, magnetic, electromagnetic and electrostatic optical systems, or any combination thereof, as appropriate for the exposure radiation being used, or for other factors, such as the use of an immersion liquid or the use of a vacuum. A vacuum environment may be used for EUV or electron beam radiation since other gases may absorb too much radiation or electrons. A vacuum environment may therefore be provided to the whole beam path with the aid of a vacuum wall and vacuum pumps.

The lithographic apparatus may be of a type having two (dual stage) or more substrate tables (and/or two or more mask tables) WT. In such "multiple stage" machines the additional substrate tables WT may be used in parallel, or preparatory steps may be carried out on one or more tables while one or more other substrate tables WT are being used for exposure.

Referring to FIGS. 1A and 1B, illuminator IL receives a radiation beam from a radiation source SO. Source SO and the lithographic apparatus may be separate entities, for example when source SO is an excimer laser. In such cases, source SO is not considered to form part of the lithographic apparatus, and radiation beam B passes from source SO to illuminator IL with the aid of a beam delivery system BD (FIG. 1B) including, for example, suitable directing mirrors and/or a beam expander. In other cases, source SO may be an integral part of the lithographic apparatus—for example when source SO is a mercury lamp. Source SO and illuminator IL, together with beam delivery system BD, if required, may be referred to as a radiation system.

Illuminator IL may include an adjuster AD (FIG. 1B) for adjusting the angular intensity distribution of the radiation beam. Generally, at least the outer and/or inner radial extent (commonly referred to as σ-outer and σ-inner, respectively)

of the intensity distribution in a pupil plane of the illuminator may be adjusted. In addition, illuminator IL may include various other components, such as an integrator IN and a condenser CO. Illuminator IL may be used to condition radiation beam B, to have a desired uniformity and intensity distribution in its cross section.

Radiation beam B is incident on the patterning device (e.g., mask MA), which is held on the support structure (e.g., mask table MT), and is patterned by the patterning device. Having traversed mask MA, radiation beam B passes through projection system PS, which focuses the beam onto a target portion C of substrate W. With the aid of second positioner PW and position sensor IF (e.g., an interferometric device, linear encoder or capacitive sensor), substrate table WT can be moved accurately, e.g. so as to position different target portions C in the path of radiation beam B. Similarly, first positioner PM and another position sensor (which is not explicitly depicted) can be used to accurately position mask MA with respect to the path of radiation beam B, e.g., after mechanical retrieval from a mask library, or during a scan.

In general, movement of mask table MT may be realized with the aid of a long-stroke module (coarse positioning) and a shod-stroke module (fine positioning), which form part of first positioner PM. Similarly, movement of substrate table WT may be realized using a long-stroke module and a short-stroke module, which form part of second positioner PW. In the case of a stepper (as opposed to a scanner) mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (known as scribe-lane alignment marks). Similarly, in situations in which more than one die is provided on mask MA, the mask alignment marks may be located between the dies.

The lithographic apparatus may be used in at least one of the following modes:

1. In step mode, support structure (e.g., mask table) MT and substrate table WT are kept essentially stationary, while an entire pattern imparted to radiation beam B is projected onto a target portion C at one time (i.e., a single static exposure). Substrate table WT is then shifted in the X and/or Y direction so that a different target portion C may be exposed.

2. In scan mode, support structure (e.g., mask table) MT and substrate table WT are scanned synchronously while a pattern imparted to radiation beam B is projected onto a target portion C (i.e., a single dynamic exposure). The velocity and direction of substrate table WT relative to support structure (e.g., mask table) MT may be determined by the (de-)magnification and image reversal characteristics of projection system PS.

3. In another mode, support structure (e.g., mask table) MT is kept substantially stationary holding a programmable patterning device, and substrate table WT is moved or scanned while a pattern imparted to radiation beam B is projected onto a target portion C. A pulsed radiation source SO may be employed and the programmable patterning device is updated as required after each movement of substrate table WT or in between successive radiation pulses during a scan. This mode of operation may be readily applied to maskless lithography that utilizes programmable patterning device, such as a programmable mirror array of a type as referred to herein.

Combinations and/or variations on the described modes of use or entirely different modes of use may also be employed.

Figure 2:
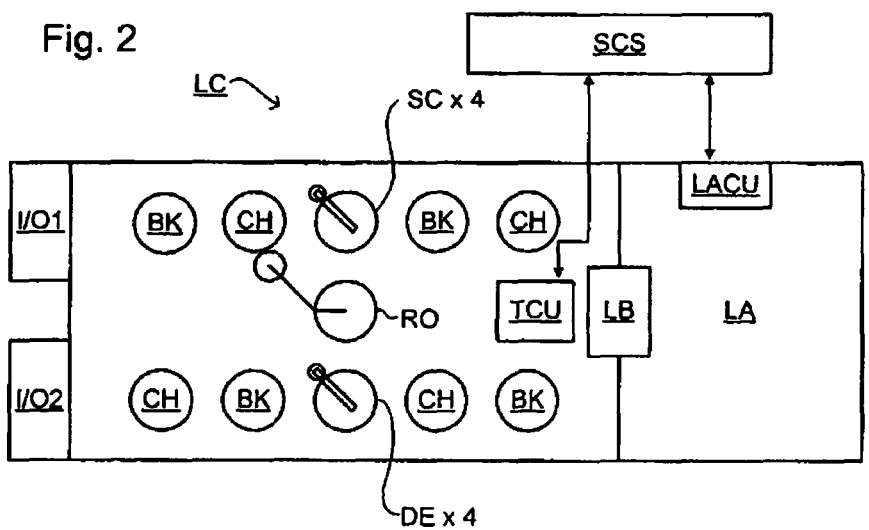
FIG. 2 depicts a lithographic cell or cluster that may be used in an embodiment of the present invention.

As shown in FIG. 2, lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into lithographic apparatus LA or lithocell LC or may be a stand-alone device. To enable most rapid measurements, it is desirable that the inspection apparatus measures properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
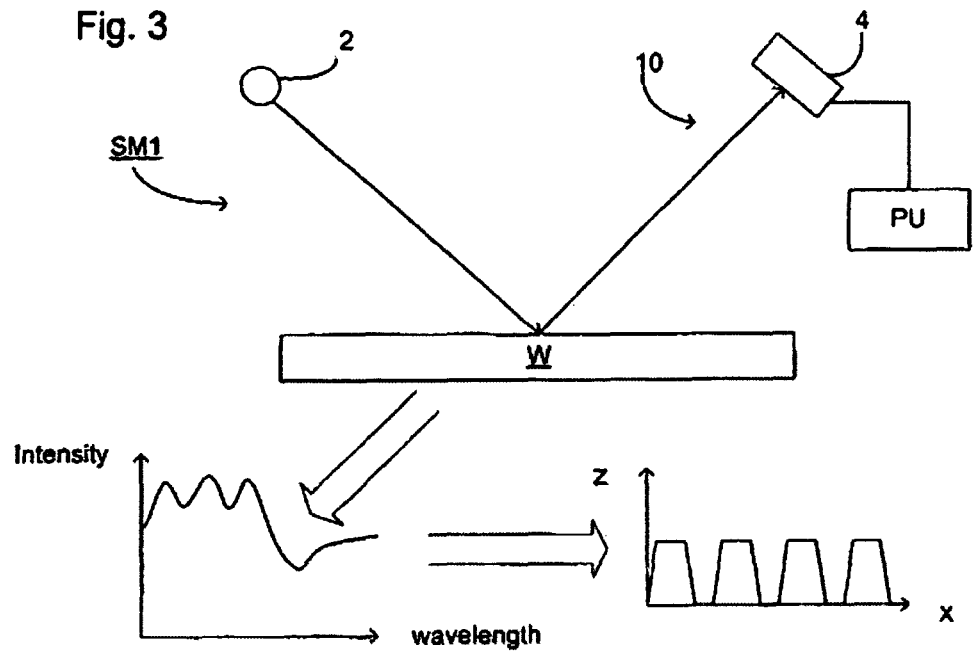
FIG. 3 depicts a first scatterometer that may be used in an embodiment of the present invention.

FIG. 3 depicts a scatterometer SM1 which may be used in embodiments of the present invention. Scatterometer SM1 includes a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
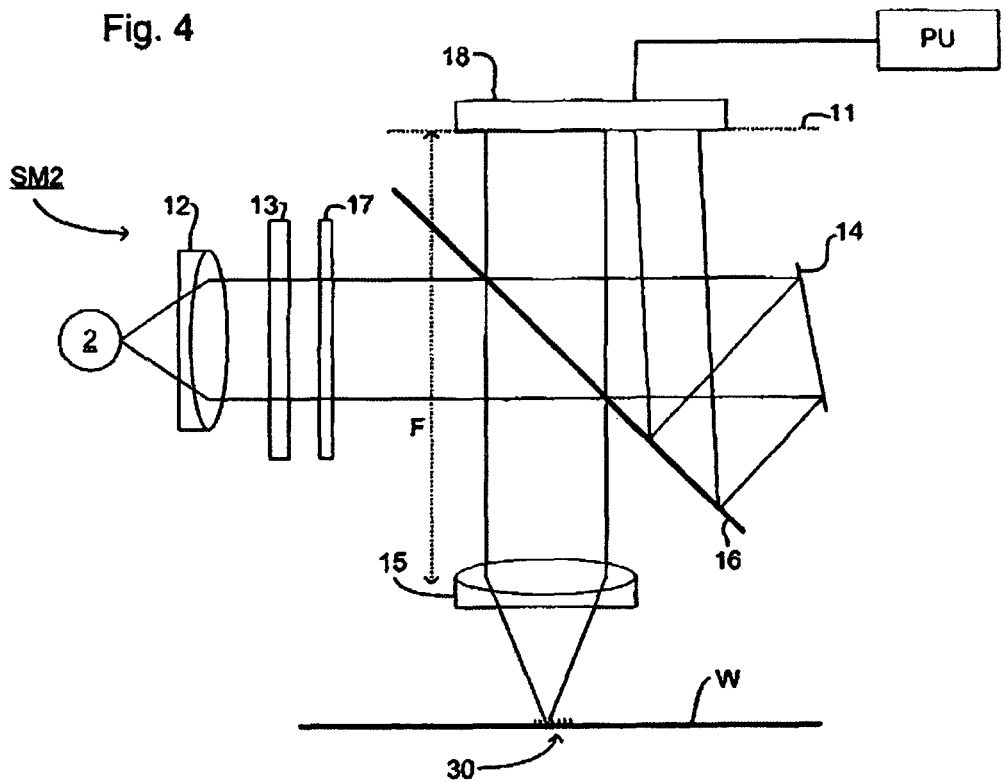
FIG. 4 depicts a second scatterometer that may be used in an embodiment of the present invention.

Another scatterometer that may be used with embodiments of the present invention is shown in FIG. 4. In scatterometer SM2, the radiation emitted by radiation source 2 is focused using lens system 12 through interference filter 13 and polarizer 17, is reflected by partially reflective surface 16 and is focused onto substrate W via a microscope objective lens 15. In an embodiment, lens 15 has a high numerical aperture (NA). In another embodiment, lens 15 has a numerical aperture of at least 0.9. In a further embodiment, lens 15 has a numerical aperture of at least 0.95. Immersion scatterometers may even have lenses with numerical apertures over 1. The reflected radiation then transmits through partially reflective surface 16 into a detector 18 in order to have the scattered spectrum detected. The detector may be located in the back-projected pupil plane 11, which is at the focal length of the lens system 15. However, the pupil plane may instead be re-imaged with auxiliary optics (not shown) onto the detector. The pupil plane is the plane in which the radial position of radiation defines the angle of incidence and the angular position defines the azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the partially reflective surface 16 the surface acts as a beam splitter, part of the incident radiation being transmitted through the beam splitter to produce a reference beam directed towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than include a set of different filters. A grating may be used instead of interference filters.

Detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ (i.e. a small proportion ($\delta$) of the wavelength ($\lambda$); e.g. of the order of 10 nm) and a spacing of at least 2 $\delta\lambda$ (i.e. twice the bandwidth). For example, wavelengths in the 495-505 nm range may be used, together with wavelengths in the 595-605 nm. Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

Substrate target 30 on substrate W may be a grating, which is printed such that after development, the bars are formed of solid resist lines. The bars may alternatively be etched into the substrate. This pattern is sensitive to chromatic aberrations in the lithographic projection apparatus, particularly projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5A:
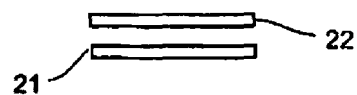
FIG. 5a depicts a cross section of a plurality of patterns according to a first embodiment of the invention.
Figure 5C:
FIG. 5c depicts a plan view of a second plurality of superimposed gratings according to a first embodiment of the invention together with the resulting diffraction pattern shown schematically.
Figure 5C:
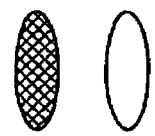
Figure 5B:
FIG. 5b depicts a plan view of a first plurality of superimposed gratings according to a first embodiment of the invention together with the resulting diffraction pattern shown schematically.
Figure 5B:

As discussed above, a plurality of superimposed gratings are used to determine the overlay error. According to the invention a plurality of sets of superimposed gratings may be superimposed on each other. A first set of superimposed gratings is used to determine a first overlay error. Later during the processing a second set of superimposed gratings are superimposed over the first set of superimposed gratings. FIGS. 5a through 5d depict a first embodiment of the invention and FIG. 5a depicts a cross section of a portion of the substrate in which a second plurality of gratings 22 is superimposed on a first plurality of gratings 21. FIG. 5b depicts a plan view of the first plurality of gratings and the resulting diffraction pattern in which the zeroth order diffraction pattern is hashed and the first order diffraction pattern is depicted as solid. FIG. 5c is a similar figure showing the second plurality of gratings and their resulting diffraction pattern. As can be seen, the gratings of the first plurality of gratings have a smaller periodicity and thus a greater distance between the zeroth and first order diffraction spots than the second plurality of gratings.

Figure 5D:
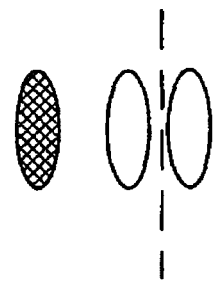
FIG. 5d is a schematic depiction of the diffraction pattern from a substrate according to a first embodiment of the invention.

A projection beam of radiation is projected onto the substrate including the two superimposed sets of gratings and the reflected radiation detected. FIG. 5d shows a schematic representation of the diffraction pattern from the two superimposed plurality of gratings. The first diffraction orders from the first and second plurality of gratings 21, 22 are in different locations. Thus by selecting the diffraction spectrum (or more particularly, just the first order) from just the second plurality of gratings it is possible to determine the overlay error from just the second plurality of gratings (the overlay error from the first plurality of gratings will have been determined before the second plurality of gratings is exposed) with no interference from the first plurality of gratings. One method of selecting just the first diffraction order from the second plurality of gratings is to detect only a limited angular range. For example, this may be achieved by setting a detection limit as shown by the dashed line by, for example, using a specific aperture. Additionally, the wavelength of the projected radiation could be varied in combination with selecting a given angular range.

The periods of the two sets of gratings must be sufficiently different to allow the diffraction orders from the second plurality of gratings to be detected without significant interference from diffraction from the first plurality of gratings. In one example, if the first set of gratings has a period of d, the second set of gratings may have a period of either greater than approximately 1.3 d or less than approximately 0.7 d. In another example, if the first set of gratings has a period of d, the second set of gratings may have a period of either greater than approximately 1.5 d or less than approximately 0.5 d. The second set of gratings may thus have a period of, for example, 1.6 d or 0.4 d. However, the period of the second set of gratings need not be an exact multiple or exactly divisible by the period of the first set of gratings.

Figure 6A:
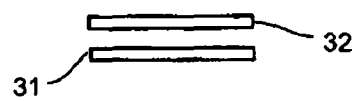
FIG. 6a depicts a cross section of a plurality of patterns according to a second embodiment of the invention.
Figure 6C:
FIG. 6c depicts a plan view of a second plurality of superimposed gratings according to a second embodiment of the invention together with the resulting diffraction pattern shown schematically.
Figure 6C:
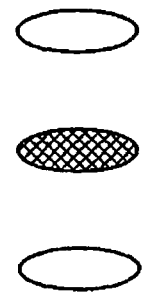
Figure 6B:
FIG. 6b depicts a plan view of a first plurality of superimposed gratings according to a second embodiment of the invention together with the resulting diffraction pattern shown schematically.
Figure 6B:
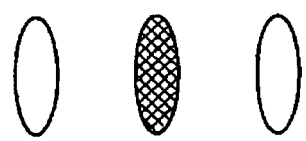
Figure 6D:
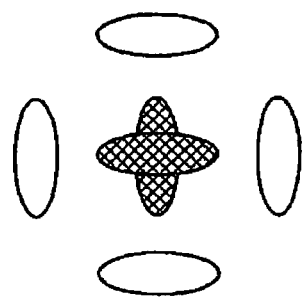
FIG. 6d is a schematic depiction of the diffraction pattern from a substrate according to a second embodiment of the invention.

FIGS. 6a through 6d depict a second embodiment of the invention in which a second plurality, or set, of gratings 32 is superimposed on a first plurality, or set, of gratings 31. As can be seen from the plan views of pluralities of gratings 32 and 31 in FIGS. 6c and 6b, the second set of gratings is perpendicular to the first set of gratings. A schematic representation of the resulting diffraction patterns is also shown in FIGS. 6b and 6c and the spread of diffraction orders from the second plurality of gratings extends perpendicularly to the spread of diffraction orders from the first plurality of gratings. The diffraction pattern resulting from projecting a beam onto the substrate with both the first and second plurality of gratings is shown in FIG. 6d. As can be seen, it is possible to select the first order of the diffraction spectrum from the first plurality of gratings from the first order of the diffraction spectrum from the second plurality of gratings to determine the overlay error in the second set of gratings. Thus for each plurality of gratings it is possible to determine the overlay error without crosstalk due to the other plurality of gratings.

Figure 7A:
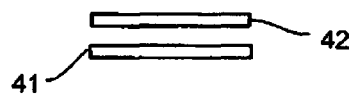
FIG. 7a depicts a cross section of each of a plurality of patterns according to a third embodiment of the invention.
Figure 7B:
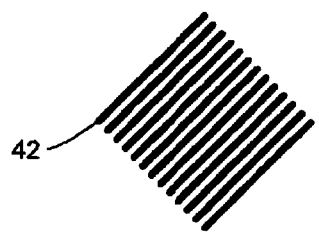
FIG. 7b is a plan view of the two gratings according to a third embodiment of the invention.

The invention is not limited to the perpendicular alignment of the two superimposed sets of gratings. FIGS. 7a and 7b show another embodiment of the present invention. In FIGS. 7a and 7b, a second plurality of gratings 42 has been superimposed over a first plurality of gratings 41. Second plurality of gratings 42 is arranged at an angle of approximately 45° to first plurality of gratings 41 so that the cross-talk between the different sets of gratings at the same lateral position is minimized. Second set of gratings 42 can be oriented at any angle or orientation which minimizes overlap and cross-talk between the two sets of gratings.

Figure 8A:
FIG. 8a depicts a cross section of each of a plurality of patterns according to a fourth embodiment of the invention.
Figure 8A:
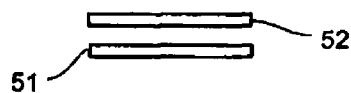
Figure 8B:
FIG. 8b is a plan view of a first set of gratings according to a fourth embodiment of the invention.
Figure 8C:
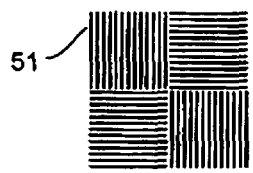
FIG. 8c is a plan view of a second set of gratings according to a fourth embodiment of the invention.

FIGS. 8a through 8c depict another embodiment of the present invention. FIG. 8a depicts a cross section of a portion of the substrate in which a second plurality of gratings 52 is superimposed on a first plurality of gratings 51. FIG. 8c depicts a first set of two superimposed gratings 51. Each grating includes four areas, two with the gratings oriented in a first direction and the other two with the gratings oriented in a second direction perpendicular to the first direction. A second set of gratings is depicted in FIG. 8b and also includes two superimposed gratings 52. Again, each grating includes four areas. However, the direction of the sub-grating of each area is perpendicular to the direction of the grating for the area over which it is superposed.

By allowing sets of gratings to be superimposed on each other use of the substrate for such targets can be greatly reduced. Although the invention has been illustrated using one dimensional gratings, it may be used in combination with other types of gratings such as honeycomb, triangular etc., although different degrees of rotation between the different sets of gratings may be required. Furthermore, the invention is not limited to just two sets of superimposed gratings. For example, using one dimensional linear gratings, a second set of gratings may be superimposed on a first set of gratings at an angle of 60°, and a third set of gratings could be superimposed over the first and second set of gratings at an angle of 60° to both sets of gratings. A third overlay error could therefore be determined using the same area of substrate.

Thus, the first order diffraction pattern from a second set of superimposed gratings may be distinguished from the first order diffraction pattern from a first set of superimposed gratings. This may be achieved by the second set having a substantially different periodicity, by having a different orientation, or any other method.

Embodiments of this invention may be used in combination with other developments to reduce scribelane usage. One example is the use of a wire grid to obscure targets. In such an example, a wire grid with a repeating pattern of less than the smallest wavelength is implanted and acts like a Faraday shield. Thus new targets can be placed on top of the wire grid and there will be no interference from targets below the wire grid.

Embodiments of the invention may be combined, for example using a second set of gratings which has a different periodicity from the first set of gratings and also oriented perpendicularly to the first set of gratings.

Although the Figures depict the use of spot illumination, embodiments of this invention may be used in combination with, for example annular illumination. The diffraction spectra will differ, but the same principles apply. If, for example, annular illumination is used the first order diffraction spectra from the different sets of superimposed gratings may not be completely distinct, but it should be possible to distinguish between them.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that embodiments of the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A substrate comprising:
   a first set of superimposed gratings and a second set of superimposed gratings, said second set of superimposed gratings in turn being superimposed over said first set of superimposed gratings, said first set of superimposed gratings having a periodicity in a first direction and said second set of superimposed gratings having a periodicity in a second direction,
   wherein said first and second directions are at an angle of between 30° and 60° to each other such that within an image of respective diffraction patterns produced by radiation reflected by each of the first set of superimposed gratings and the second set of superimposed gratings, the diffraction patterns of at least one order corresponding to each of the first and second sets of superimposed gratings are spatially distinguishable from each other within said image.

2. A method of measuring a property of a substrate, said method comprising:
   exposing a first grating;
   exposing a second grating superimposed over said first grating to form a first set of gratings with said first grating, said first set of gratings having a periodicity in a first direction;
   exposing a third grating;
   exposing a fourth grating superimposed over said third grating to form a second set of gratings with said third grating, said second set of gratings having a periodicity in a second direction;
   projecting radiation onto said second set of gratings;
   detecting said radiation reflected by said substrate to form a detected image; and
   determining said property from said reflected radiation,
   wherein said second set of gratings is superimposed on said first set of gratings and said first and second directions are at an angle of between 30° and 60° to each other such that within said detected image in respective diffraction patterns produced by radiation reflected by each of the first set of superimposed gratings and the second set of superimposed gratings, the diffraction patterns of at least one order corresponding to each of the first and second sets of superimposed gratings are spatially distinguishable from each other within said image.

3. An inspection apparatus configured to measure a property of a substrate, the apparatus comprising:
   a radiation projector configured to project radiation onto said substrate:
   a high numerical aperture lens;
   a detector configured to detect the radiation beam reflected from a surface of the substrate; and
   a substrate comprising a first set of superimposed gratings and a second set of superimposed gratings, said second set of superimposed gratings being superimposed over said first set of superimposed gratings, said first set of superimposed gratings having a periodicity in a first direction and said second set of superimposed gratings having a periodicity in a second direction wherein said first and second directions are at an angle of between 30° and 60° to each other such that such that within an image of respective diffraction patterns produced by radiation reflected by each of the first set of superimposed patterns and the second set of superimposed gratings, the diffraction patterns of at least one order corresponding to each of the first and second sets of superimposed gratings are spatially distinguishable from each other within said image.

4. A substrate comprising:
   a first set of superimposed gratings; and
   a second set of superimposed gratings,
   wherein said second set of superimposed gratings in turn being superimposed over said first set of superimposed gratings, said first set of superimposed gratings having a periodicity in a first direction and said second set of superimposed gratings having a periodicity in a second direction wherein said first and second directions are at an angle of between 30° and 60° to each other.

5. A substrate comprising:
   a first set of superimposed gratings; and
   a second set of superimposed gratings, the second set of superimposed gratings in turn being superimposed over the first set of superimposed gratings, the first set of superimposed gratings having a periodicity in a first direction and the second set of superimposed gratings having a periodicity in a second direction; and
   a third set of superimposed gratings, the third set of superimposed gratings in turn being superimposed over the second set of superimposed gratings, the third set of superimposed gratings having a periodicity in a third direction,
   wherein the first and second directions are at an angle of 60° to each other and the third direction is at an angle of 60° to the first and second directions.

* * * * *